(12) United States Patent
Iguchi et al.

(10) Patent No.: US 7,850,921 B2
(45) Date of Patent: Dec. 14, 2010

(54) DISPENSER, REAGENT DISPENSER AND SAMPLE ANALYZER

(75) Inventors: Satoshi Iguchi, Kobe (JP); Takashi Yamato, Kakogawa (JP); Nobuhiro Kitagawa, Akashi (JP); Akio Toyoda, Kobe (JP)

(73) Assignee: Sysmex Corporation, Kobe (JP)

( * ) Notice: Subject to any disclaimer, the term of this patent is extended or adjusted under 35 U.S.C. 154(b) by 606 days.

(21) Appl. No.: 11/893,919

(22) Filed: Aug. 17, 2007

(65) Prior Publication Data

US 2008/0044311 A1 Feb. 21, 2008

(30) Foreign Application Priority Data

Aug. 18, 2006 (JP) .............................. 2006-223276
Jul. 31, 2007 (JP) .............................. 2007-198586

(51) Int. Cl.
*B01L 3/02* (2006.01)
*G01N 21/00* (2006.01)
*G01N 31/00* (2006.01)
*G01N 33/00* (2006.01)
*G01N 1/22* (2006.01)

(52) U.S. Cl. .......................... 422/100; 422/63; 422/67; 422/99; 73/863.11

(58) Field of Classification Search .................. None
See application file for complete search history.

(56) References Cited

U.S. PATENT DOCUMENTS

| | | | | |
|---|---|---|---|---|
| RE30,730 E | * | 9/1981 | Duff | 422/64 |
| 5,178,019 A | * | 1/1993 | Keiter | 73/863.11 |
| 5,646,046 A | * | 7/1997 | Fischer et al. | 436/49 |
| 6,021,253 A | * | 2/2000 | Bell | 392/338 |
| 6,727,480 B2 | * | 4/2004 | Fernando et al. | 219/549 |
| 2003/0032191 A1 | * | 2/2003 | Hilson et al. | 436/47 |
| 2004/0122559 A1 | * | 6/2004 | Young et al. | 700/269 |
| 2007/0274870 A1 | * | 11/2007 | Hochstrasser et al. | 422/100 |

FOREIGN PATENT DOCUMENTS

JP 2004-061173 2/2004

* cited by examiner

*Primary Examiner*—Jill Warden
*Assistant Examiner*—Charles Hammond
(74) *Attorney, Agent, or Firm*—Brinks Hofer Gilson & Lione

(57) ABSTRACT

The present invention is to present a dispenser which is capable of heating a liquid to an approximately constant temperature in the same time regardless of an aspiration amount of the liquid. The dispenser comprises a liquid holder for holding a liquid; aspiration amount information obtaining means for obtaining aspiration amount information indicating an aspiration amount of the liquid; an aspiration-discharge part for aspirating the aspiration amount of the liquid indicated by the obtained aspiration amount information into the liquid holder and discharging the liquid from the liquid holder; a heater for heating the liquid held by the liquid holder; a temperature sensor for detecting a temperature of the liquid held by the liquid holder; target temperature determining means for determining a target temperature of the liquid based on the aspiration amount of the liquid indicated by the obtained aspiration amount information; and controlling means for controlling the heater so as to conform the temperature detected by the temperature sensor to the target temperature.

24 Claims, 10 Drawing Sheets

US 7,850,921 B2

DISPENSER, REAGENT DISPENSER AND SAMPLE ANALYZER

RELATED APPLICATIONS

This application claims priority under 35 U.S.C. §119 to Japanese Patent Application No. 2006-223276 filed Aug. 18, 2006 and Japanese Patent Application No. 2006-198586 filed Jul. 31, 2007, the entire content of which is hereby incorporated by reference.

FIELD OF THE INVENTION

The present invention relates to a dispenser, a reagent dispenser and a sample analyzer.

BACKGROUND OF THE INVENTION

When measuring and analyzing a sample such as blood and urine, reagent is generally added to the sample to prepare a measurement sample and the measurement sample is measured to obtain optical characteristics and the like. In blood coagulation measurement, the sample is heated for a predetermined time mainly to stabilize and promote the blood coagulation reaction.

For example, blood coagulation measuring apparatuses heat a blood sample to a predetermined temperature (usually 37° C.) for a predetermined time, and thereafter dispense reagent such as PT reagent and APTT reagent to the sample to prepare a measurement sample. And blood coagulation time is obtained by measuring the optical density of the measurement sample. When the measurement sample is measured, it is desired that the measurement sample is kept under a warm condition in order to stabilize and promote the blood coagulation reaction. However, reagent is kept under a low temperature (normally about 10° C.) before dispensing the reagent to a sample. Therefore, when a cool reagent is dispensed to a heated sample, a temperature of the sample drops and the blood coagulation reaction may not proceed normally.

A heating pipette provided with a heater for heating aspirated reagent is disclosed in, for example, Japanese Patent Laid-Open Publication No. 2004-61173. This kind of heating pipette heats aspirated reagent after setting a target temperature (for example 37° C.), and dispenses the heated reagent to a sample.

However, there are several measurement items in blood coagulation measurement, and a type of reagent and aspiration amount of the reagent vary by the measurement item. Moreover, required degree of heating is influenced by an environmental temperature. Therefore, it is difficult to heat all reagents to a temperature in a predetermined range. If a large amount of reagent is aspirated, even when a target temperature of the reagent is set at 37° C., the reagent may not be heated sufficiently and be discharged in a temperature lower than 37° C. On the other hand, if a small amount of reagent is aspirated, even when a target temperature of the reagent is set at 37° C., the reagent may be heated excessively and be discharged in a temperature exceeding 37° C.

Furthermore, it is necessary to make a space of an opening of a reagent container as small as possible to prevent evaporation of expensive reagent. And it is necessary to decrease an external diameter of the heating pipette which is inserted into the opening of the reagent container when the space of the opening is decreased. It is considered that the reagent container is slightly tilted in order to reduce the reagent dead volume (the amount of unaspiratable liquid remaining at the bottom of the container) and in order to effectively aspirate the reagent within the reagent container by the heating pipette. In this instance, however, the space of the opening decreases when viewed from above (an space which is obtained by projecting an actual opening space on a horizontal plane) as a result of tilting the opening of the reagent container relative to the horizontal plane. Therefore, it is desired to decrease the external diameter of the heating pipette inserted into the opening when the heating pipette is inserted in a vertical direction. The heating pipette is configured by providing a heater inside a long cylindrical pipette. It is difficult to decrease the external diameter of the pipette unless the size of the heater is decreased. When the size of the heater is decreased, the heating capability of the heater becomes less. Therefore, a longer time is necessary to attain the target temperature of 37° C., thus failing to meet the need for high speed processing.

SUMMARY OF THE INVENTION

A first aspect of the present invention is a dispenser, comprising: a liquid holder for holding a liquid; aspiration amount information obtaining means for obtaining aspiration amount information indicating an aspiration amount of the liquid; an aspiration-discharge part for aspirating the aspiration amount of the liquid indicated by the obtained aspiration amount information into the liquid holder and discharging the liquid from the liquid holder; a heater for heating the liquid held by the liquid holder; a temperature sensor for detecting a temperature of the liquid held by the liquid holder; target temperature determining means for determining a target temperature of the liquid based on the aspiration amount of the liquid indicated by the obtained aspiration amount information; and controlling means for controlling the heater so as to conform the temperature detected by the temperature sensor to the target temperature.

A second aspect of the present invention is a reagent dispenser, comprising: reagent type information obtaining means for obtaining reagent type information indicating a type of a reagent to be dispensed; a reagent pipette for holding the reagent; an aspiration-discharge part for aspirating the reagent into the reagent pipette and discharging the reagent from the reagent pipette; a heater for heating the reagent held by the reagent pipette; a temperature sensor for detecting a temperature of the reagent held by the reagent pipette; target temperature determining means for determining a target temperature of the reagent based on the type of the reagent indicated by the obtained reagent type information; and controlling means for controlling the heater so as to conform the temperature detected by the temperature sensor to the target temperature.

A third aspect of the present invention is a sample analyzer, comprising: a sample dispenser for dispensing a sample into a container; a reagent dispenser for dispensing a reagent into the container to prepare a measurement sample from the sample and the reagent; aspiration amount determining means for determining an aspiration amount of the reagent; and a detector for detecting optical information from the measurement sample, wherein the reagent dispenser comprises: a reagent pipette for holding the reagent; an aspiration-discharge part for aspirating the aspiration amount of the reagent determined by the aspiration amount determining means into the reagent pipette and discharging the reagent from the reagent pipette; a heater for heating the reagent held by the reagent pipette; a temperature sensor for detecting a temperature of the reagent held by the reagent pipette; target temperature determining means for determining a target temperature of the reagent based on the aspiration amount of the reagent determined by the aspiration amount determining means; and controlling means for controlling the heater so as to conform the temperature detected by the temperature sensor to the target temperature.

DESCRIPTION OF THE PREFERRED EMBODIMENTS

The preferred embodiment of the present invention is described hereinafter based on the drawings.

[General Structure of the Sample Analyzer]

The general structure of a sample analyzer 1 of an embodiment of the present invention is described below.

The sample analyzer 1 is an apparatus for optically measuring and analyzing the amount and activity level of specific substances related to coagulation and fibrinolytic function of blood, and uses blood (plasma) as a sample. The sample analyzer 1 performs optical measurement (main measurement) of a sample using a coagulation time method, synthetic substrate method, and immunoturbidity method. The coagulation time method used in the present embodiment detects and measures the change in the transmission light during the sample coagulation process. Measurement item include PT (prothrombin time), APTT (active partial thromboplastin time), and Fbg (fibrinogen content) and the like. Measurement item of the synthetic substrate method include ATIII and the like, and measurement item of the immunoturbidity method include D-dimer, FDP and the like.

Figure 1:
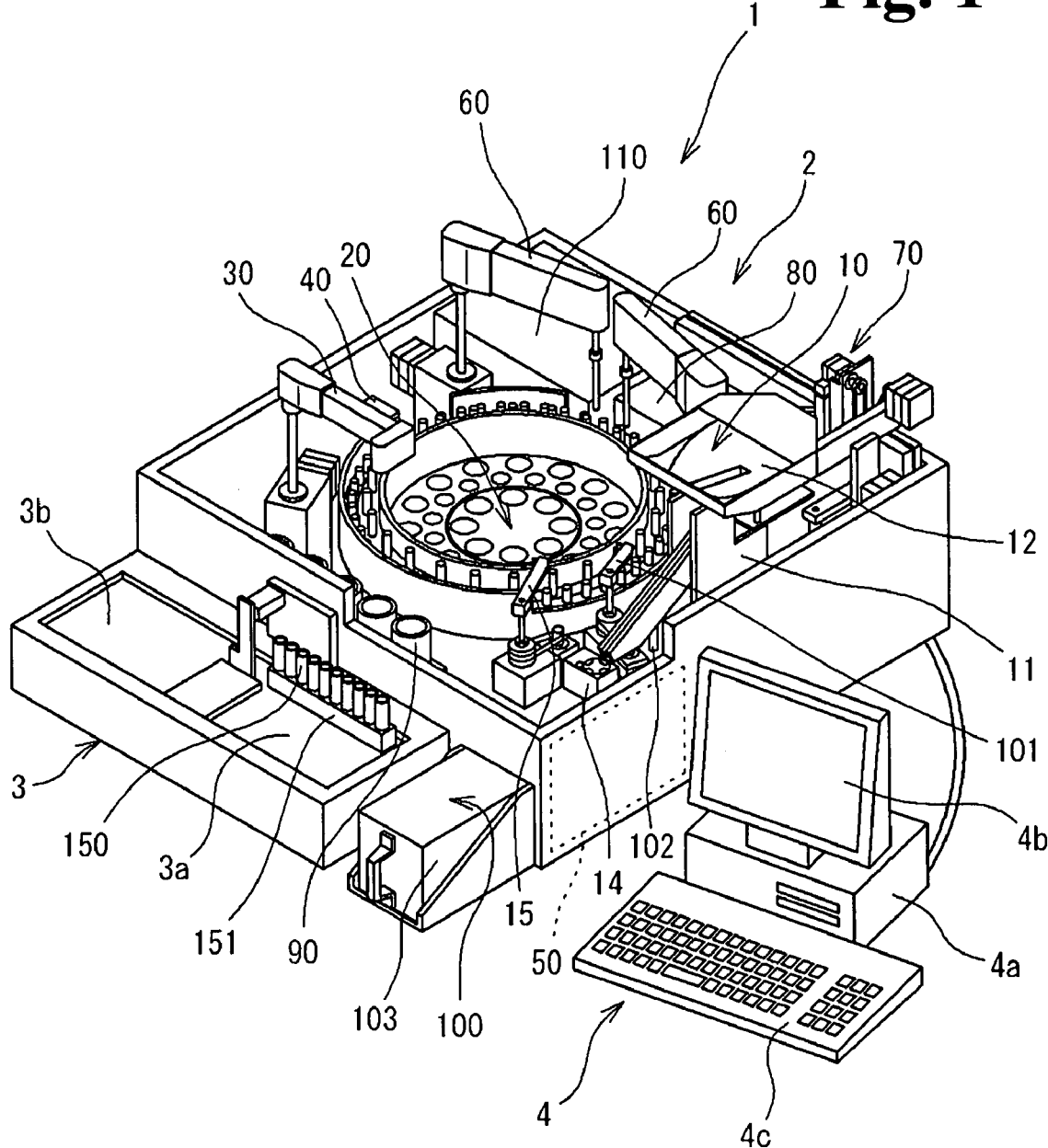
FIG. 1 is a perspective view showing the overall structure of an embodiment of the sample analyzer of the present invention.

As shown in FIG. 1, the sample analyzer 1 is mainly configured by a measuring unit 2, transporting unit 3 disposed on the front side of the measuring unit 2, and a control device 4 which is electrically connected to the measuring unit 2. The measuring unit 2 is provided with a controller 25 (refer to FIG. 5) for controlling the operation of each of the units in the measuring unit 2 and transporting unit 3. Although the transporting unit 3 and measuring unit 2 are integrated as one part of the analyzer 1 in the present embodiment, the transporting unit 3 may also be separate from the sample analyzer 1. For example, a large scale system that includes a plurality of analyzers may employ a mode in which the many analyzers are connected to a large scale transport line without providing a transport section for each analyzer.

The control device 4 is configured by a personal computer 401 (PC), and includes a controller 4a, display 4b, and keyboard 4c, as shown in FIG. 1. The controller 4a functions to control the operations of the measuring unit 2 and transporting unit 3, and analyzes the optical information of samples obtained by the measuring unit 2. The controller 4a is configured by a CPU, ROM, RAM and the like. Furthermore, the display 4b is provided to display information relating to interference substances (hemoglobin, chyle (fats), bilirubin) present in a sample, and analysis results obtained by the controller 4a.

Figure 3:
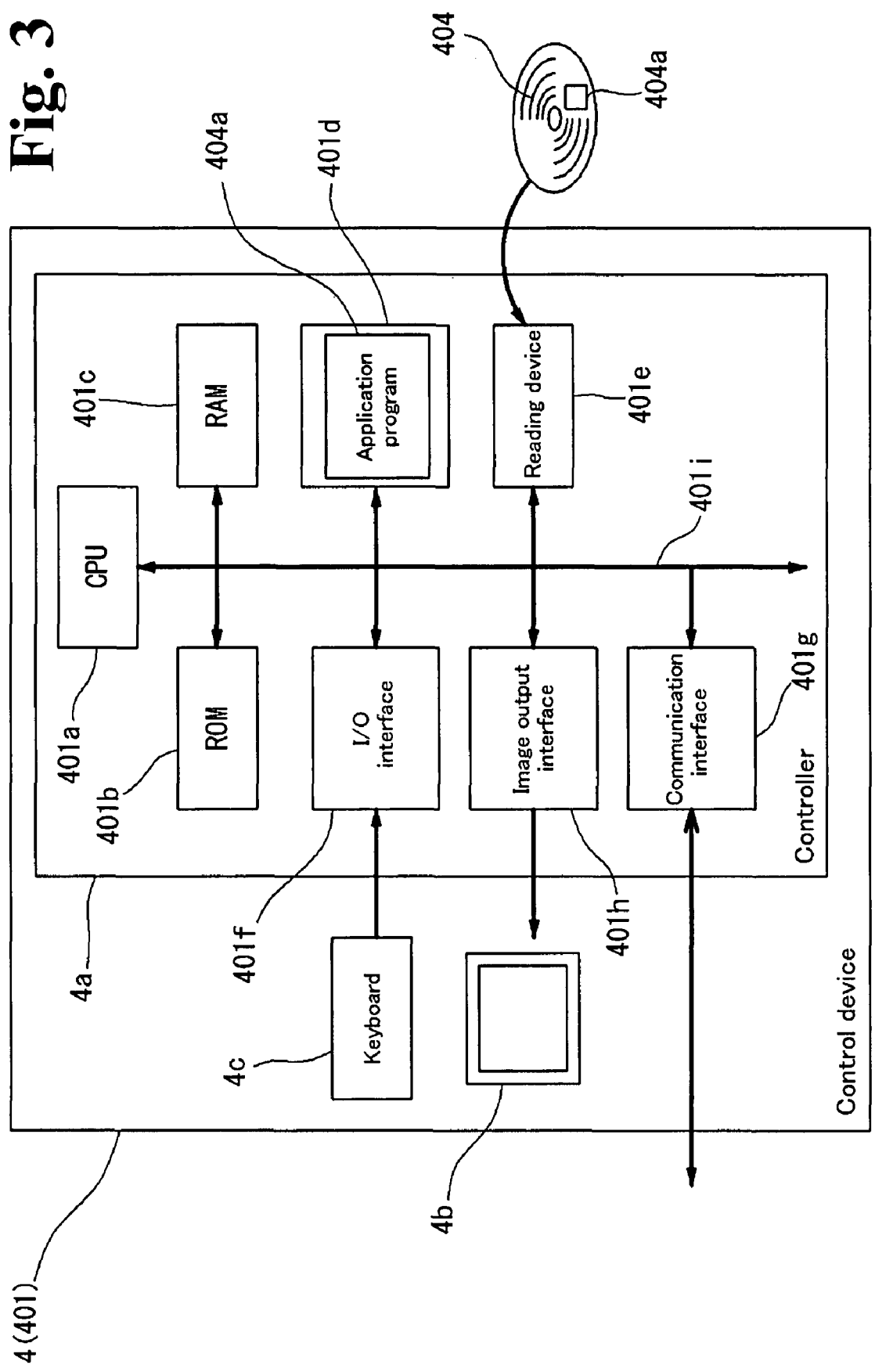
FIG. 3 is a block diagram of the control device of the sample analyzer shown in FIG. 1.

The structure of the control device 4 is described below. As shown in FIG. 3, the controller 4a is mainly configured by a CPU 401a, ROM 401b, RAM 401c, hard disk 401d, reading device 401e, I/O interface 401f, communication interface 401g, and image output interface 401h. The CPU 401a, ROM 401b, RAM 401c, hard disk 401d, reading device 401e, I/O interface 401f, communication interface 401g, and image output interface 401h are connected by a bus 401i.

The CPU 401a is capable of executing computer programs stored in the ROM 401b, and computer programs loaded in the RAM 401c. The computer 401 functions as the control device 4 when the CPU 401a executes an application program 404a which is described later.

The ROM 401b is configured by a mask ROM, PROM, EPROM, EEPROM or the like, and stores computer programs executed by the CPU 401a and data and the like used in conjunction therewith.

The RAM 401c is configured by SRAM, DRAM or the like. The RAM 401c is used when reading the computer program recorded in the ROM 401b and on the hard drive 401d. The RAM 401c is further used as a work area of the CPU 401a when these computer programs are being executed.

The hard drive 401d contains various installed computer programs to be executed by the CPU 401a such as an operating system and application programs and the like, as well as data used in the execution of these computer programs. Also installed on the hard disk 401d in the present embodiment is the application program 404a used to calculate the presence and concentration of interference substances.

The reading device 401e is configured by a floppy disk drive, CD-ROM drive, DVD-ROM drive or the like, and is capable of reading the computer programs and data stored on a portable recording medium 404. Furthermore, the portable recording medium 404 may also store the application program 404a in the present embodiment, such that the computer 401 is capable of reading the application program 404a from the portable recording medium 404 and installing the application program 404a on the hard disk 401d.

Not only may the application program 404a be provided by the portable recording medium 404, it also may be provided from an external device connected to the computer 401 so as to be capable of communication over the electric communication line (wire line or wireless). For example, the application program 404a may be stored on the hard disk of a server computer connected to the internet, such that the computer 401a can access the server computer and download the application program 404a, and then install the application program 404a on the hard disk 401d.

Also installed on the hard disk 401d is an operating system providing a graphical user interface environment, such as, for example, Windows (registered trademark) produced and sold by Microsoft Corporation, U.S.A. In the following description, the application program 404a of the present embodiment operates on such an operating system.

The I/O interface 401f is configured by a serial interface such as a USB, IEEE1394, RS232C or the like, parallel interface such as SCSI, IDE, IEEE1284 or the like, analog interface such as a D/A converter, A/D converter or the like. The keyboard 4c is connected to the I/O interface 401f, such that a user can input data in the computer 401 using the keyboard 4c.

The communication interface 401g is, for example, and Ethernet (registered trademark) interface. The computer 401 can send and receive data to and from the measuring unit 2 using a predetermined communication protocol via the communication interface 401g.

The image output interface 401h is connected to the display 4b configured by an LCD, CRT or the like, such that image signals corresponding to the image data received from the CPU 401a can be output to the display 4b. The display 4b displays images (screens) in accordance with the input image signals.

The transporting unit 3 functions to transport a rack 151 that holds a plurality (ten in the present embodiment) of test tubes 150 that contain samples to the aspirating position 2a (refer to FIG. 2) of the measuring unit 2 to supply sample to the measuring unit 2. Furthermore, the transporting unit 3 has a rack set region 3a that accommodates the racks 151 that hold the test tubes 150 containing unprocessed samples, and a rack receiving region 3b that accommodates the racks 151 that hold test tubes 150 containing processed samples.

The measuring unit 2 is capable of obtaining optical information related to a supplied sample by optically measuring the sample supplied from the transporting unit 3. In the present embodiment, a sample is dispensed from the test tube 150 disposed in the rack 151 of the transporting unit 3 into a cuvette 152 (refer to FIG. 2) of the measuring unit 2, and is then optically measured. Furthermore, the measuring unit 2 is provided with a cuvette supplier 10, rotating part 20, sample dispensing arm 30 as a sample dispensing section, HIL detecting part 40, lamp unit 50, two reagent dispensing arms 60 as a reagent dispensing section, cuvette transporter 70, detecting part 80, emergency sample acceptor 90, cuvette disposal part 100, and fluid flow section 110, as shown in FIGS. 1 and 2.

The cuvette supplier 10 is configured to sequentially supply a plurality of cuvettes 152 which have been directly inserted to a hopper 12 by a user to the rotating part 20. As shown in FIG. 2, the cuvette supplier 10 includes a hopper 12 mounted on the device body via a bracket 11 (refer to FIG. 1), two induction plates 13 provided below the hopper 12, support base 14 disposed at the bottom end of the two induction plates 13, and a catcher 15 provided at a predetermined distance from the support base 14. The two induction plates 13 are disposed so as to be mutually parallel with a space therebetween so the space is smaller than the diameter of the flange of the cuvette 152 and larger than the diameter of the barrel of the cuvette 152. The cuvettes 152 which have been supplied into the hopper 12 are configured so as to move smoothly while dropping toward the support base 14 with the flange engaged at the top surface of the two induction plates 13. Furthermore, the support base 14 functions to rotate the cuvette 152 that has dropped between the induction plates 13 to a position at which the cuvette 152 can be grabbed by the catcher 15. The catcher 15 is provided to supply the cuvette 152, which has been moved by the support base 14, to the rotating part 20.

The rotating part 20 is provided to transport in a circular direction those cuvettes 152 which have been received from the cuvette supplier 10, as well as reagent containers (not shown in the drawings) accommodating reagent to be added to the sample in the cuvette 152. The rotating part 20 is provided with a cover (not shown in the drawing) to enclose the rotating part 20, and has the function of storing the reagent containers under low temperature (approximately 10° C.) refrigeration. Deterioration of the reagent is prevented by storing the reagent at low temperature. As shown in FIG. 2, the rotating part 20 is configured by a circular reagent table 21, annular reagent table 22 disposed on the outer side of the circular reagent table 21, annular secondary dispensing table 23 disposed on the outer side of the circular reagent table 22, and annular primary dispensing table 24 disposed on the outer side of the circular secondary dispensing table 23. The primary dispensing table 24, secondary dispensing table 23, and reagent tables 21 and 22 are configured so as to be mutually and independently rotatable in both clockwise and counter clockwise directions.

Figure 2:
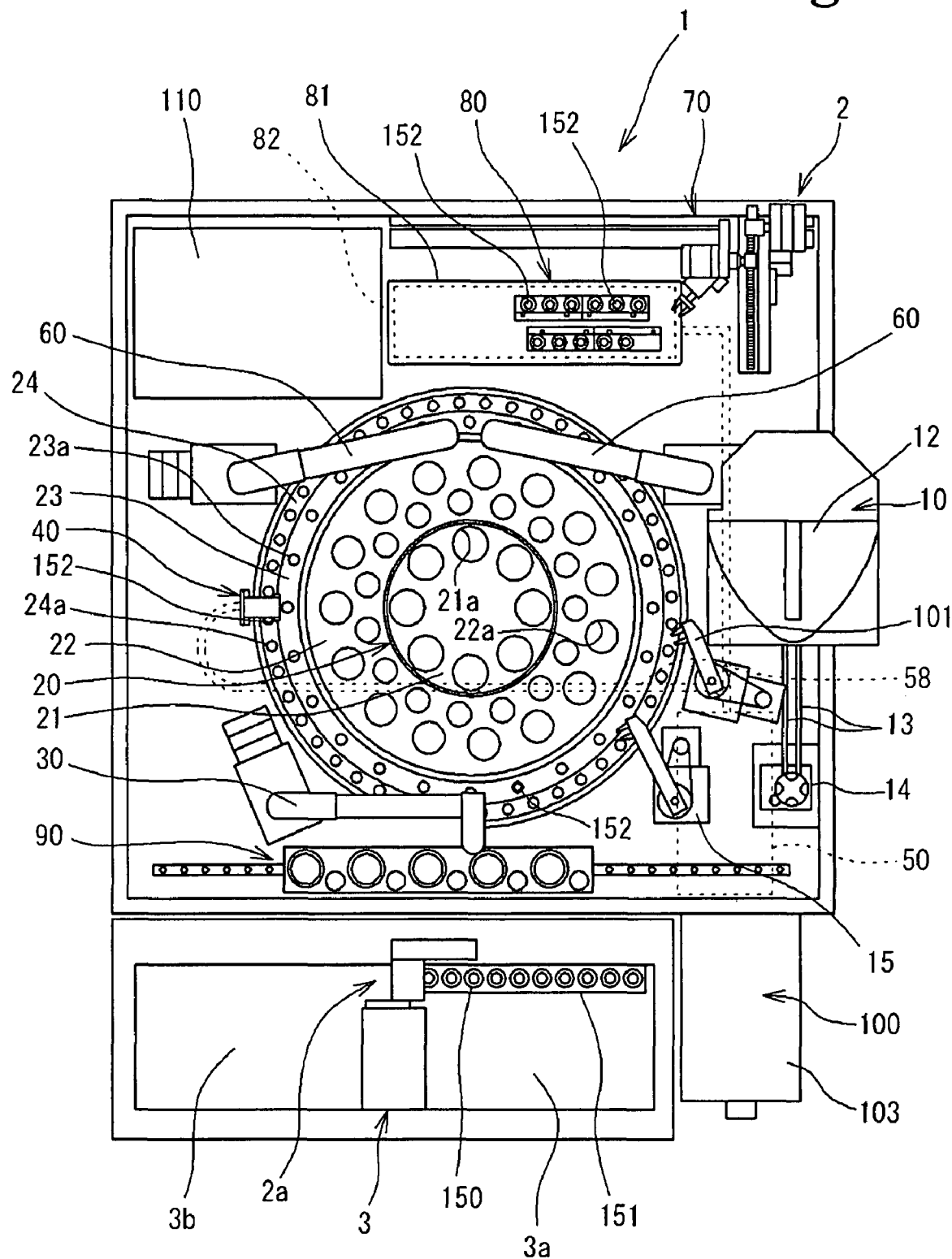
FIG. 2 is a top view showing the detection section and transport section of the sample analyzer of FIG. 1.

As shown in FIG. 2, the reagent tables 21 and 22 respectively include a plurality of holes 21a and 22a provided at predetermined spacing in the circumferential direction. The holes 21a and 22a of the reagent tables 21 and 22 are provided to load a plurality of reagent containers (not shown in the drawings) that hold various reagents to be added when preparing measurement samples from samples. Furthermore, the primary dispensing table 24 and secondary dispensing table 23 respectively include a plurality of cylindrical holders 24a and 23a provided at predetermined spacing in the circumferential direction. The holders 24a and 23a are provided to hold the cuvettes 152 received from the cuvette supplier 10. A sample contained in a test tube 150 of the transport device 3 is dispensed to a cuvette 152 held by the holder 24a of the primary dispensing table 24 in a primary dispensing process. Furthermore, a sample contained in the cuvette 152 loaded in the primary dispensing table 24 is dispensed to a cuvette 152 loaded in the holder 23a of the secondary dispensing table 23 in a secondary dispensing process. A pair of holes are formed in the holder 24a at mutually facing positions on the sides of the holder 24a. The pair of holes 24b are provided for the passage of light emitted from a beam splitter optical fiber 58 of the lamp unit 50 described later.

The sample dispensing arm 30 functions to both aspirate a sample contained in a test tube 150 transported to the aspiration position 2a via the transport device 3, and to dispense the aspirated sample into a cuvette 152 transported to the rotating part 20.

The HIL detecting part 40 is configured so as to acquire optical information from a sample in order to measure the presence and concentration of interference substances (chyle, hemoglobin, bilirubin) in the sample before adding reagent. Specifically, the presence and concentrations of interference substances are measured using four types of light (405 nm, 575 nm, 660 nm, 800 nm) among five types of light (340 nm, 405 nm, 575 nm, 660 nm, 800 nm) emitted from the lamp unit 50 described later. The 405 nm wavelength light is absorbed by chyle, hemoglobin, and bilirubin. That is, chyle, hemoglobin, and bilirubin influence the optical information measured using light at a wavelength of 405 nm. Furthermore, light at a wavelength of 575 nm is absorbed by chyle and hemoglobin, although this light is essentially is not absorbed by bilirubin. That is, chyle and hemoglobin influence the optical information measured using light at a wavelength of 575 nm. Light at wavelengths of 660 nm and 800 nm are absorbed by chyle, although these wavelengths essentially are not absorbed by bilirubin and hemoglobin. That is, chyle influences the optical information measured using light at wavelengths of 660 nm and 800 nm. Chyle absorbs light from the low wavelength region 405 nm to the high wavelength region 800 nm, with chyle absorbing more light at the 660 nm wavelength than at the 800 nm wavelength. That is, the optical information measured using light at the 800 nm wavelength is less influenced by chyle than optical information at the 660 nm wavelength.

The acquisition of sample optical information by the HIL detecting part 40 is performed before optically measuring (main measurement) the sample by the detecting part 80. As shown in FIG. 2, the HIL detecting part 40 obtains optical information from the sample within the cuvette 152 held by the holder 24a of the primary dispensing table 24.

In the present embodiment, the lamp unit 50 is provided to supply light to be used in the optical measurements performed by the HIL detecting part 40 and the detecting part 80, as shown in FIG. 2. That is, a single lamp unit 50 is configured so as to be used commonly by the HIL detecting part 40 and the detecting part 80.

Figure 10:
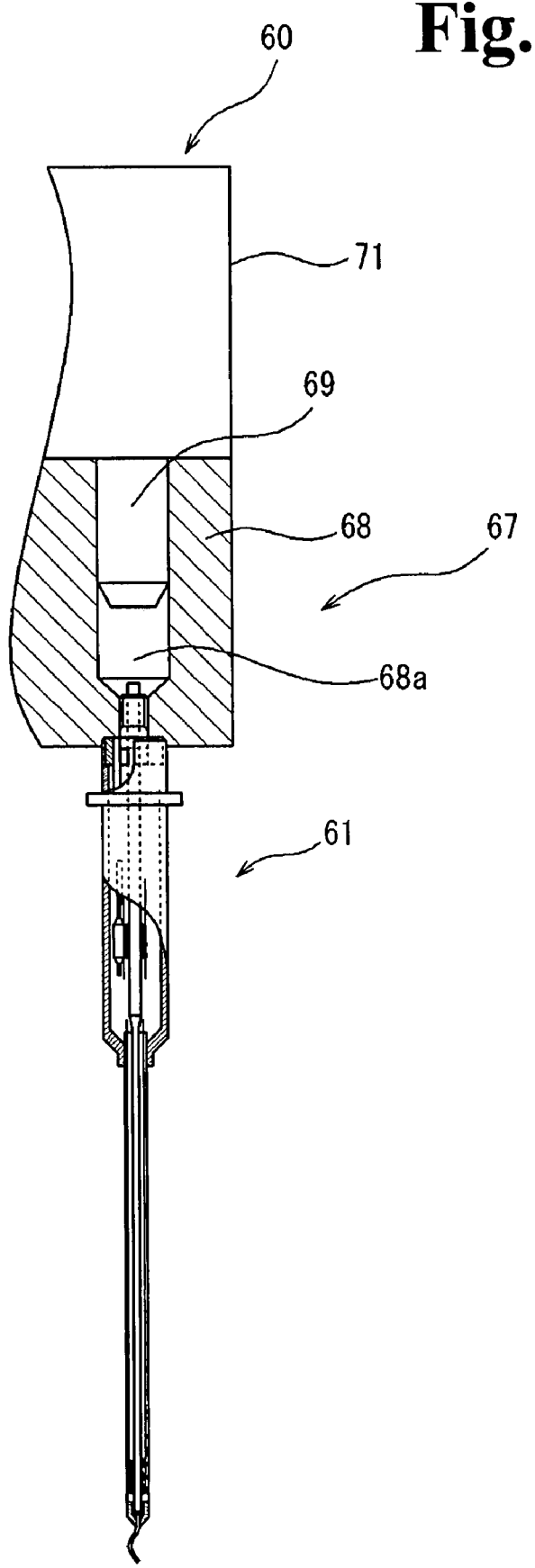
FIG. 10 is a vertical section view showing the structure of the reagent dispensing arm.

As shown in FIGS. 1 and 2, the reagent dispensing arm 60 is provided to dispense the reagent within a reagent container (not shown in the drawings) loaded on the rotating part 20 into a cuvette 152 held in the rotating part 20. In this way a measurement sample is prepared by adding reagent to a sample after the sample has been optically measured by the HIL detecting part 40. The cuvette transporter 70 is provided to move the cuvette 152 between the rotating part 20 and the detecting part 80. As shown in FIG. 10, a heating pipette 61, which configures a dispensing device with a heating function, is mounted on the tip of the reagent dispensing arm 60, and the heating pipette 61 is connected to a syringe pump 67 disposed within the reagent dispensing arm 60. The syringe pump 67 is provided with a cylinder 68, a piston 69 which is inserted in a hole 68a of the cylinder 68, and a linear actuator 71. The linear actuator 71 reciprocatingly moves the piston 69 within the hole 68a of the cylinder 68 by a built-in stepping motor.

The detecting part 80 functions to heat the measurement sample prepared by adding reagent to a sample, and measure optical information from the measurement sample. As shown in FIG. 2, the detecting part 80 is configured by a cuvette loader 81, and a detector 82 disposed below the cuvette loader 81.

As shown in FIGS. 1 and 2, the emergency sample acceptor 90 is provided to perform a sample analysis process on sample requiring immediate processing. The emergency sample acceptor 90 is capable of performing an interrupt on behalf of an emergency sample when there is an on-going sample analysis process being performed on a sample supplied from the transport device 3. The cuvette disposal 100 is provided to dispose of cuvettes 152 from the rotating part 20. As shown in FIG. 2, the cuvette disposal part 100 is configured by a cuvette waste unit 101, disposal hole 102 provided at predetermined spacing from the cuvette waste unit 101 (refer to FIG. 1), and waste box 103 provided below the disposal hole 102. The cuvette waste unit 101 is provided to move a cuvette 152 from the rotating part 20 to the waste box 103 via the disposal hole 102 (refer to FIG. 1). A fluid flow section 110 is provided to supply a fluid such as cleaning liquid to a nozzle provided on each dispensing arm during the shutdown process of the blood coagulation analyzer 1.

[Structure of the Dispensing Device with a Heating Function]

The dispensing device with a heating function of the present embodiment is configured by a heating pipette 61 which is capable of aspirating and discharging reagent, a heater for heating the reagent aspirated by the heating pipette 61, and a controller 25 for controlling the temperature of the heater to conform the temperature of the aspirated reagent to a target temperature. The controller 25 is provided with a CPU 25a, flash memory 25b, RAM 25c and the like.

Figure 4:
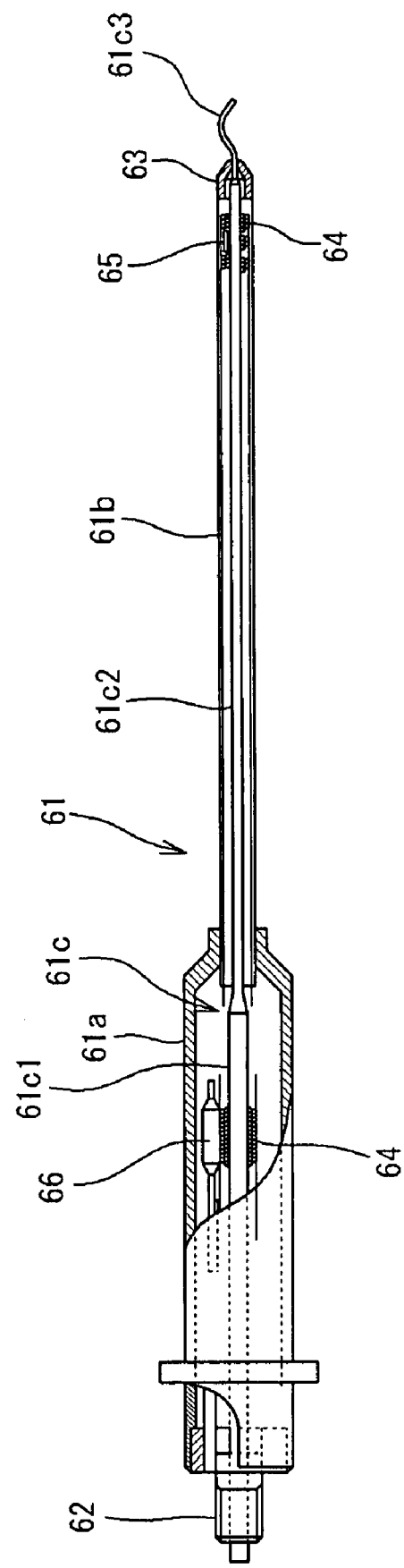
FIG. 4 is a section view in the axial direction showing an example of a heating pipette.

As shown in FIG. 4, the heating pipette 61 has an overall cylindrical shape, and is configured by a nozzle case 61a which has a large diameter on the side mounted on the dispensing arm 60, a nozzle pipe 61b that has a small diameter on the tip side that has an opening for aspirating and discharging reagent, and a pipette 61c disposed within the nozzle case 61a and nozzle pipe 61b.

A male threaded part 62 is formed at one end of the nozzle case 61a, and the heating pipette 61 is mounted on the reagent dispensing arm 60 by screwing the male threaded part 62 into a female threaded part (not shown in the figure) formed on the reagent dispensing arm 60. The other end of the nozzle case 61a has a reduced diameter, and the nozzle pipe 61b is inserted into this reduced diameter part and fixed therein. A sleeve cap 63 is inserted in the inner circumference of the tip of the nozzle pipe 61b, and fixed therein.

The pipette 61c is configured by a large diameter section 61c1 disposed within the nozzle case 61a, a small diameter section 61c2 disposed within the nozzle pipe 61b, and an injection-discharge section 61c3 disposed at the tip of the small diameter section 61c2. The tip side of the large diameter section 61c1 has a reduced diameter and is connected to the small diameter section 61c2 and, similarly, the tip side of the small diameter section 61c2 also has a reduced diameter and is connected to injection-discharge section 61c3. The injection-discharge section 61c3 has an arc shaped configuration so as to discharge reagent obliquely downward from the tip of the injection-discharge section 61c3 such that the reagent impinges the inner wall of the cuvette and falls along the inner wall when reagent is dispensed into the cuvette. Therefore, reagent is not dispensed directly into the sample within the cuvette, and air bubble generation is prevented. When air bubbles are generated in a sample, the disturbance produced by the air bubbles prevents accurate optical measurement, and sample analysis accuracy declines.

A heating wire 64, which configures a heater for heating the reagent aspirated and held in the pipette 61c, is wound around the outer circumference of the large diameter section 61c1 and small diameter section 61c2 (excluding the approximately 3 mm of the tip) of the pipette 61c. A thermistor 65 is disposed near the tip of the small diameter section 61c2 of the pipette 61c to detect the temperature of the reagent within the pipette 61c, and a temperature fuse 66 is disposed on the outer circumference of the heating wire 64 wound around the large diameter section 61c1 of the pipette 61c to prevent overheating of the heating wire 64. The heating wire 64 is not wound on the injection-discharge section 61c3 due to structural limitations in the present embodiment.

The reagent held in the pipette 61c is heated by a current flowing through the heating wire 64. In the present embodiment, the controller 25, which controls the temperature of the heating wire 64, adjusts the target temperature of the heating wire 64 in accordance with the amount of aspirated reagent (the amount of reagent held in the pipette 61c). Although the controller 25 for controlling the temperature of the heating wire 64 is provided on the measuring unit 2 side in the present embodiment, the controller 25 may also be included in the controller 4a of the previously mentioned control device 4.

The dispensing device with a heating function of the present embodiment is configured so as to control the amount of heat generated by the heating wire 64 by adjusting the target temperature of the heating wire 64 in accordance with the amount of aspirated reagent. Therefore, variation in the time necessary to heat reagent to a predetermined temperature can be prevented, that is, reagent can be heated to an approximately constant temperature in the same time regardless of whether the amount of aspirated reagent increases or decreases.

Figure 7:
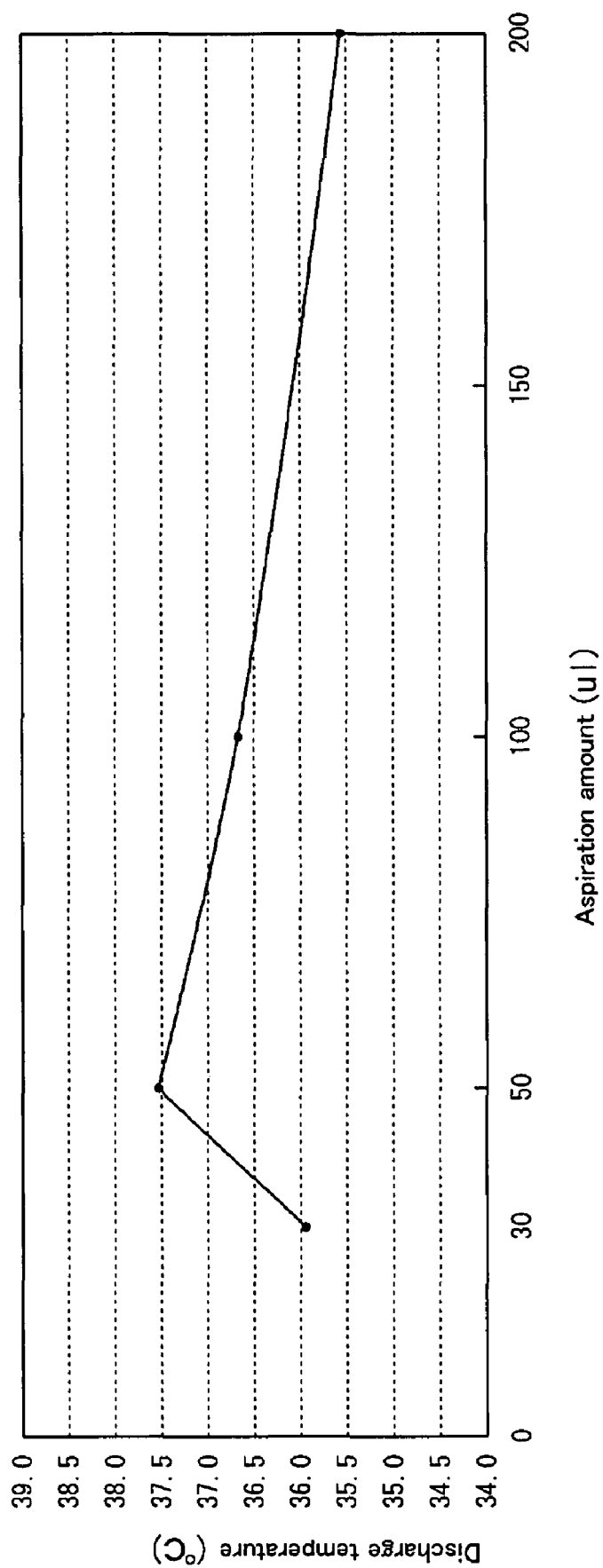
FIG. 7 shows an example of a relationship between an aspiration amount of a reagent and a temperature of the reagent when the reagent is discharged in a conventional heating pipette.

FIG. 7 shows an example of a relationship between the amount of aspirated reagent and a temperature of the reagent when the reagent is discharged in a conventional heating pipette (the structure of the pipette and heating wire, but excluding the structure of the controller, is the same as shown in FIG. 4) in which the target temperature is fixed regardless of the amount of aspirated reagent, that is, the target temperature of the heating wire 64 is not adjusted in accordance with the amount of aspirated reagent. In this example, the reagent temperature before aspiration is 10° C., and the heating time was three seconds. Although the target temperature is set at 37° C., the reagent temperature when the reagent is discharged peaks (approximately 37.6° C.) at an aspiration amount of 50 μL, and the reagent temperature decreases regardless of whether the aspiration amount increases or decreases and in most cases the reagent temperature is different from the target temperature, as the figure makes clear. When a large amount of reagent is aspirated, the heating time ends before the target temperature is attained (that is, before a steady condition is reached) because the time from aspiration to discharge of the reagent is fixed, and as a result, the reagent temperature when the reagent is discharged is lower than the target temperature. However, when the amount of aspirated reagent is less than a predetermined amount (50 μL in the example shown in FIG. 7), a large percentage of the total amount of reagent can not be heated by the heating wire (the heating wire is not disposed around injection-discharge section 61c3 nor the tip of the small diameter section 61c2 of the pipette). Therefore, the reagent temperature when the reagent is discharged decreases as the aspiration amount decreases.

Figure 8:
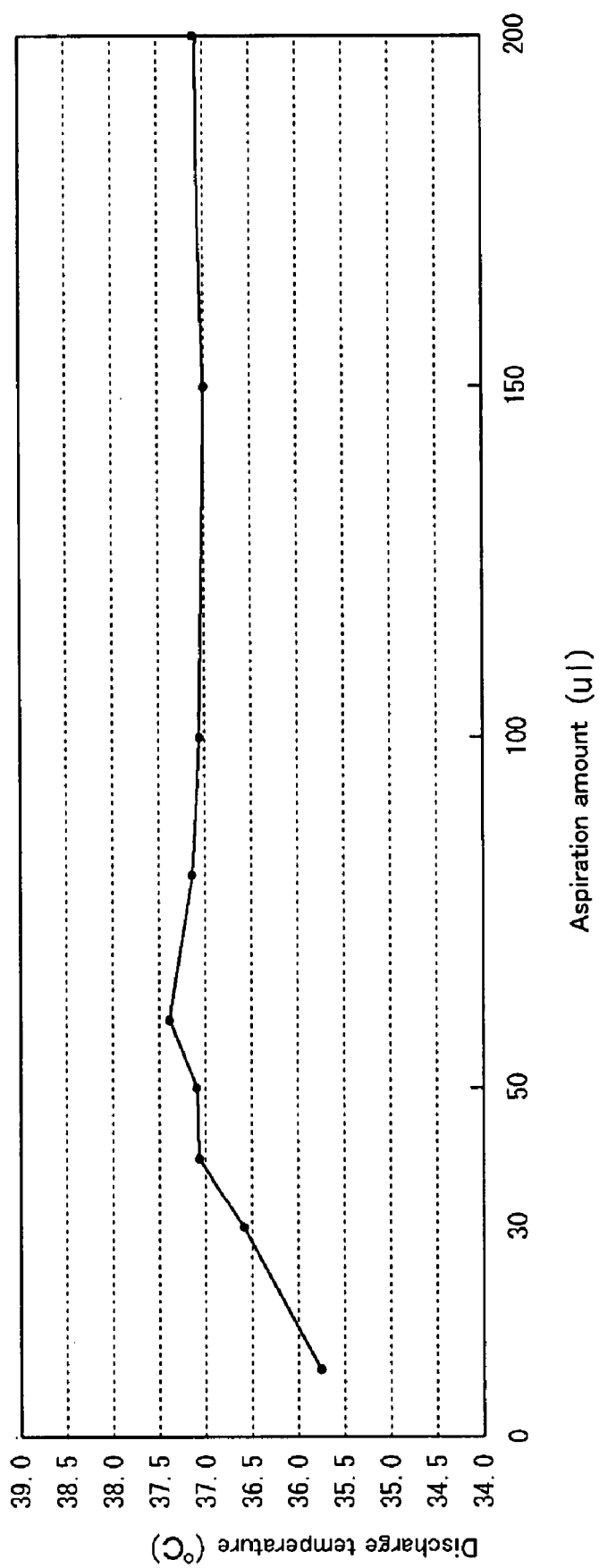
FIG. 8 shows a relationship between an aspiration amount of a reagent and a temperature of the reagent when the reagent is discharged in the heating pipette of the present invention.

On the other hand, the dispensing device with a heating function of the present embodiment can substantially standardize the reagent temperature when the reagent is discharged since the target temperature is adjusted in accordance with the amount of aspirated reagent, as shown in FIG. 8. In the example shown in FIG. 8, the reagent temperature before aspiration is 110° C., and the heating time was three seconds. In this example, the target temperature is changed before aspirating the reagent, and the reagent is discharged after the heating wire has attained a steady condition. Furthermore, the target temperature is set at 37° C. when the aspiration amount is 100 μL, and the target temperature is adjusted as shown in Table 1 below when the aspiration amount is otherwise.

In Table 1, [control amount] refers to the amount proportional to a voltage value applied to the heating wire; the control amount when the reagent temperature attains 37° C. after the 100 μL of 10° C. reagent has been heated for three seconds is set at a standard control amount (=1), and a ratio to this standard control amount is shown in the table. As the control amount increases, the target temperature is set higher.

TABLE 1

| | aspiration amount (μL) | | | | | | | | |
|---|---|---|---|---|---|---|---|---|---|
| | 10 | 30 | 40 | 50 | 60 | 80 | 100 | 150 | 200 |
| control amount | 1.15 | 1.07 | 1.03 | 0.986 | 0.989 | 0.994 | 1 | 1.01 | 1.04 |

In the example shown in FIG. 8, the target temperature of the heating wire is set higher as the aspiration amount exceeds the standard amount of 100 μL (the control amount is set higher). Although the heating speed decreases as the reagent temperature approaches the target temperature (as the differential decreases between the reagent temperature and the target temperature) in the proportional control and PID control methods of the present embodiment, the heating temperature also may not decrease as the actual target temperature is approached by setting the target temperature of the heating wire high compared to when the target temperature of the heating wire is not set high. As a result, a large amount of heat is applied to a large amount of reagent, such that the reagent can be heated to a fixed temperature (approximately 37° C.) in a heating time of three seconds even when there is a large amount of reagent.

Furthermore, when the aspiration amount is less than a predetermined amount of approximately 45 μL below the standard value (100 μL), the target temperature of the heating wire is set higher as the aspiration amount decreases. The reason for this temperature increase is that a large percentage of the total amount of reagent can not be heated by the heating wire when the aspirated amount of reagent is less than a predetermined amount as previously described in relation to the example of FIG. 7, and as a result, the reagent temperature when the reagent is discharged decreases as the aspiration amount decreases when the target temperature remains constant.

Temperature control of the heating pipette is described in detail below.

Figure 5:
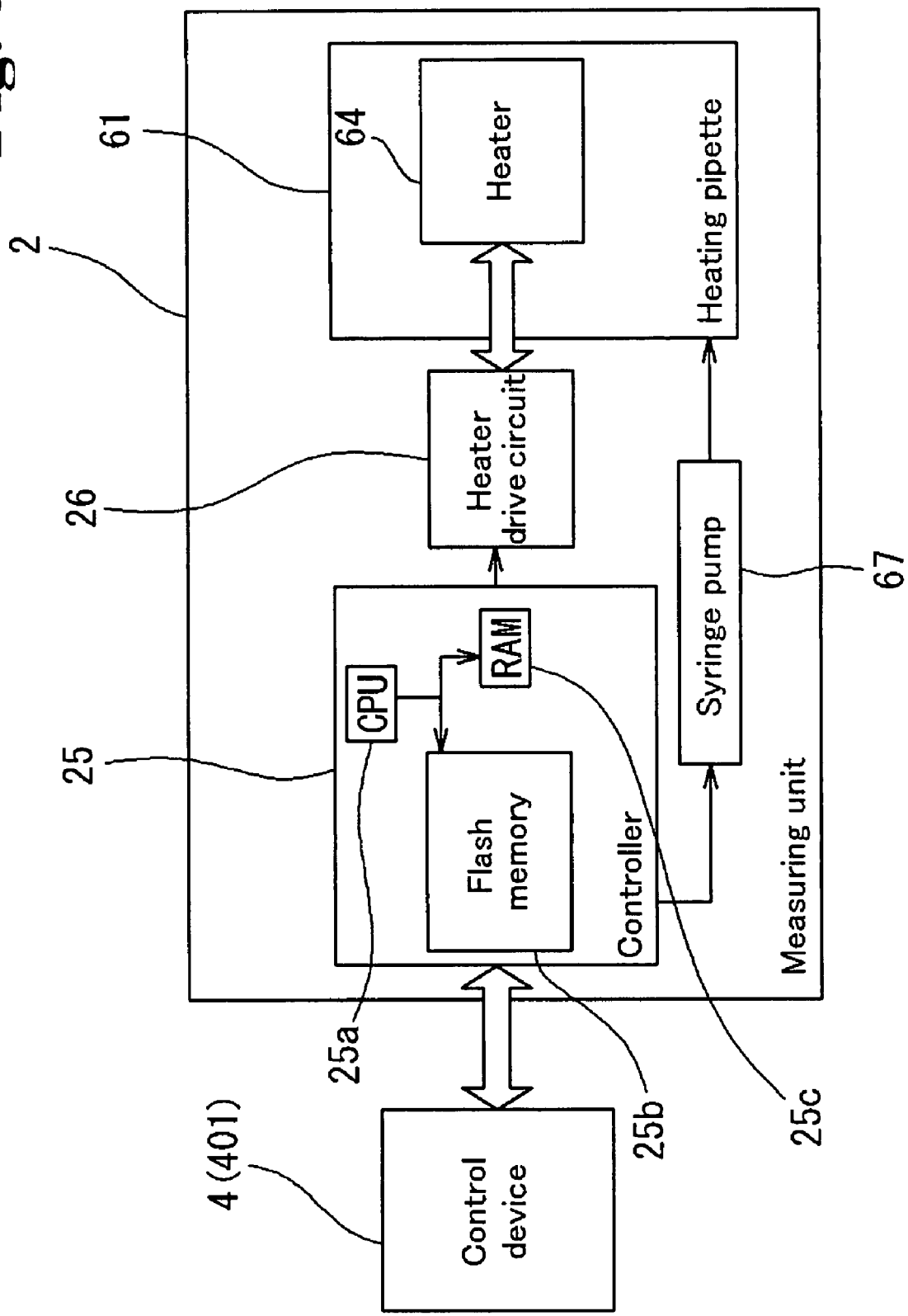
FIG. 5 illustrates the heating pipette controller.
Figure 6:
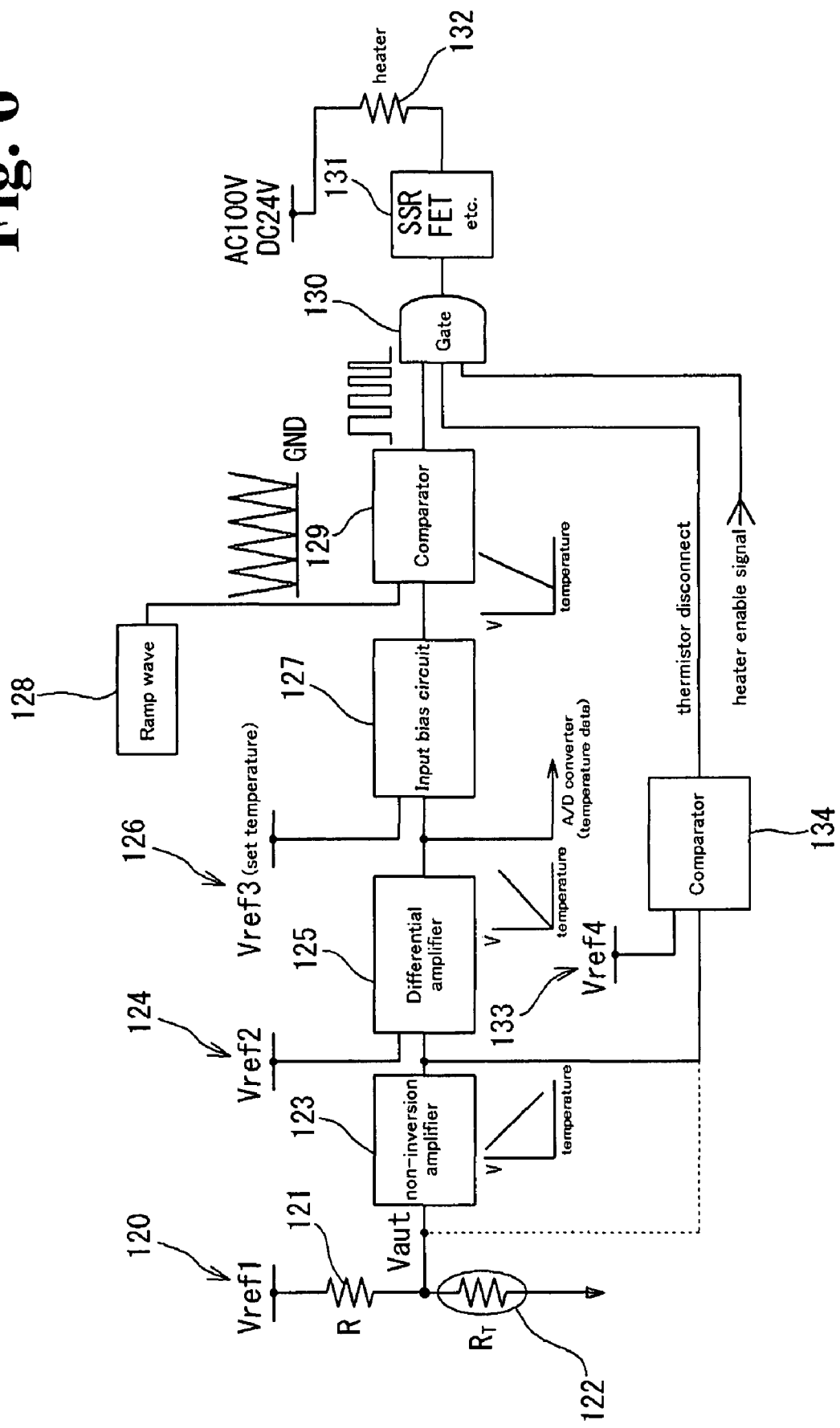
FIG. 6 shows the heater drive circuit of the heating pipette.

FIG. 5 illustrates the controller of the heating pipette of the present embodiment, and FIG. 6 shows the heater drive circuit 26 of the heating pipette. The controller of the heating pipette 61 is configured by the controller 25 of the previously described measuring unit 2, and the controller 25 fulfills the role of controlling the temperature of the heater 64 so as to heat the aspirated reagent to a target temperature.

As shown in FIG. 6, in the heater drive circuit 26, a first standard voltage 120 is supplied to a voltage divider circuit configured by a predetermined resistor 121 and a resistor 122 of the thermistor 65, and the difference between the partial voltage of the resistor 122 that has passed through a non-inversion amplifier 123 is amplified by a differential amplifier 125. The difference between the output from the differential amplifier 125 and a third standard voltage 126 that corresponds to a set temperature (target temperature) is calculated by an input bias circuit 127, and in a comparator 129 a block pulse corresponding to the current flow time of the heater 132 is generated by the pulse width of a pulse width control using a ramp wave generator 128. The current flow to the heater 132 is controlled by the ON/OFF operation of a switching means 131 in accordance with the generated block wave. The difference between the partial voltage of the resistor 122 of the thermistor 65 is normally monitored in the comparator 134. The resistor 122 becomes infinite when the thermistor 65 is disconnected, and as a result the current flow to the heater 132 is blocked by the AND circuit function of a gate 130 when the voltage difference exceeds a threshold value and when a heater enable signal is output.

In the example shown in FIG. 8, therefore, heating of the reagent ends before the reagent temperature attains a steady condition. In the case of normal feedback control, when a large amount of reagent is aspirated, much time elapses before the reagent temperature attains a target temperature in accordance with the amount and a steady condition is reached. However, the reagent can be heated to a target temperature in a short time by adjusting the target temperature in accordance with the reagent amount, and ending the heating of the reagent before the reagent temperature attains a steady condition. For example, since there is a difference up to 38° C. even when the actual target temperature of 37° C. is approached when a large amount of reagent is aspirated, a duty ratio pulse signal corresponding to this difference can be generated by the comparator 129 by setting the target temperature in a feedback controller so as to be set higher as the amount of aspirated reagent increases (set at 38° C. which is higher than the actual reagent target temperature (37° C.). Thus, the amount of heat generated by the heater 132 is controlled in accordance with the amount of reagent, and the reagent target temperature of 37° C. can be attained within a limited time. That is, the target temperature is attained in the middle of approaching the steady temperature condition (transition time).

In the present embodiment, the heating wire controller 25 can adjust the target temperature according to the amount of aspirated reagent to be used in a measurement. The amount of reagent used is determined by the type of reagent used in blood coagulation analysis. Relational expressions representing the relationship between the amount of reagent and the target temperature are pre-stored in the flash memory 25b of the controller 25, and the controller 25 can adjust the target temperature according to the amount of reagent used for a measurement based on the relational expressions stored in the flash memory 25b. When PT is measured, for example, 50 μL of plasma is heated for three minutes, 100 μL of PT reagent is dispensed to the plasma, and thereafter the PT measurement is performed. When measuring APTT, 50 μL of plasma is heated for one minute, 50 μL of APTT reagent is dispensed to the plasma and heated for two minutes, after which 50 μL of calcium chloride solution (20 mM or 25 mM) is dispensed and the APTT measurement is performed. Thus, the controller 25 can adjust the target temperature according to the amount of aspirated reagent used in a measurement by pre-storing the relationship between the amount of aspirated reagent and the target temperature in the flash memory 25b. Therefore, reagent that has been heated to a fixed temperature can be discharged from the heating pipette even when the type of reagent has changed.

Since the reagent temperature is affected by the environmental temperature when reagent is dispensed to a sample, the environmental temperature may be considered when setting the heating wire target temperature. Since two parameters that include the environmental temperature and the amount of aspirated reagent are involved in the target temperature in this case, the target temperature may be expressed, for example, by a primary equation in which the two parameters are variables, then the target temperature can be simply determined from the amount of aspirated reagent and the environmental temperature.

[Sample Analysis Process]

The sample analysis operation performed by the above sample analyzer 1 is described briefly below.

Figure 9:
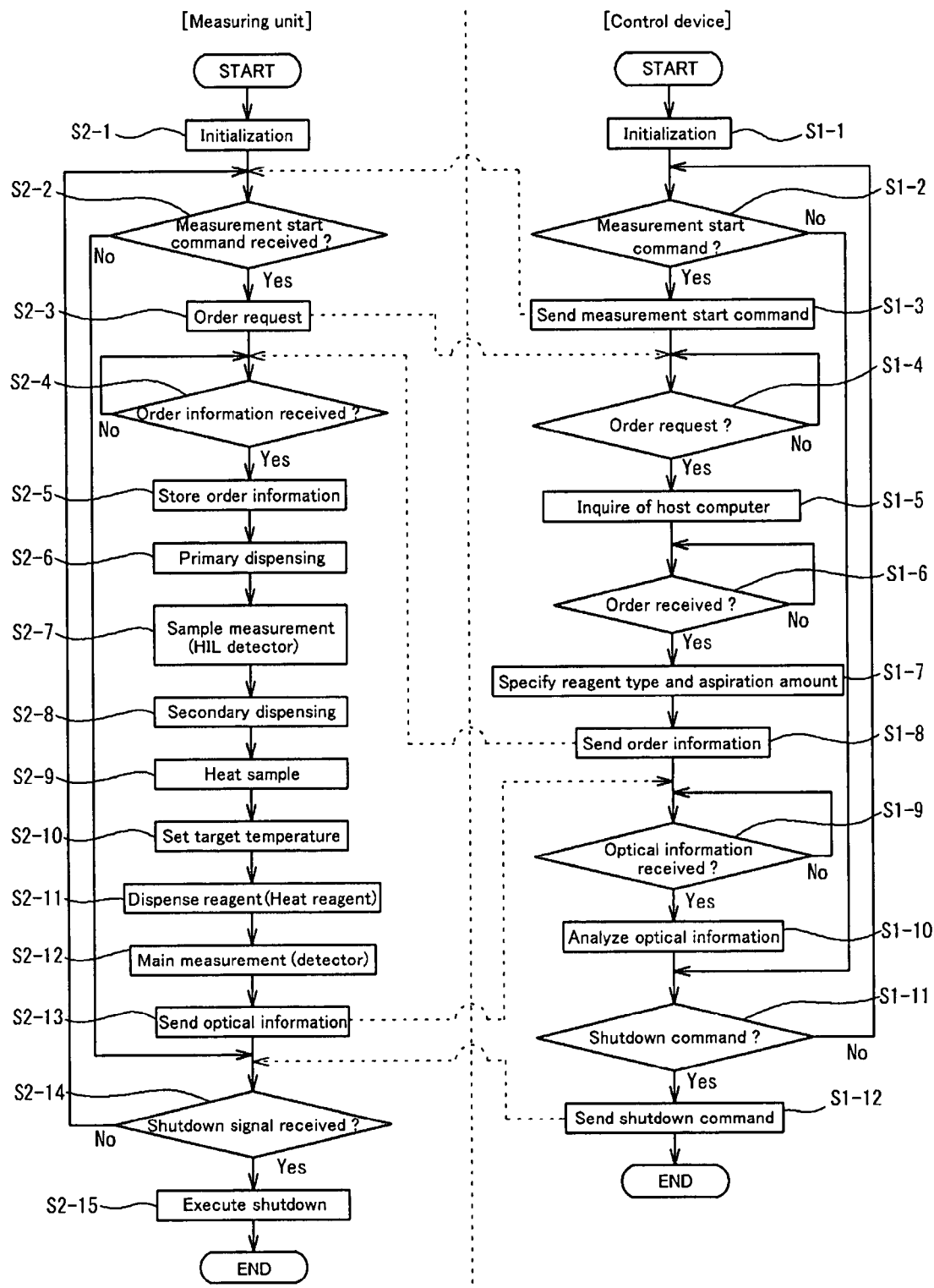
FIG. 9 is a flow chart showing the sequence of the sample analysis operation of the sample analyzer of FIG. 1.

FIG. 9 is a flow chart showing the sequence of the sample analysis operation of the sample analyzer of FIG. 1. First, the measuring unit 2 and control device 4 are initialized by respectively turning ON the power sources of the measuring unit 2 and control device 4 shown in FIG. 1 (step S1-1, S2-1). In this way, an operation is performed to return each dispensing arm and the mechanism that moves the cuvettes 152 to the initial positions, and software stored in the controller 4a of the control device 4 is initialized.

Then, the CPU 401a of the control device 4 determines whether or not a measurement start command has been received from the operator (step S1-2), and when such a measurement start command has been received the measurement start command is sent to the controller 25 of the measuring unit 2 (step S1-3). When a measurement start command has not been received, the CPU 401a jumps to the process of step S1-11.

Then, the CPU 25a of the measuring unit 2 determines whether or not a measurement start command has been received from the CPU 401a (step S2-2). When a measurement start command has been received, the CPU 25a controls the transporting unit 3 as shown in FIG. 2, and after the rack 151 loaded with test tubes 150 containing samples (blood plasma) has been moved to a position corresponding to the aspiration position 2a, the CPU 25a controls a barcode reader (not shown in the drawing) provided in the measuring unit 2 to read the barcodes adhered to each test tube 150. Thereafter, the CPU 25a requests order information corresponding to the sample ID represented in the barcode to the control device 4 (step S2-3).

Next, the CPU 401a of the control device 4 determines whether or not an order information request has been received from the CPU 25a (step S1-4). When an order information request has been received, the CPU 401a issues an inquiry of order information including sample analysis item to a not shown host computer (a computer which stores information regarding samples, patients and sample-by-sample analysis item, and manages the stored information) which is connected to the control device 4 over a network, based on the sample ID represented in the barcode (step S1-5). Then, the CPU 401a determines whether or not order information that includes analysis item has been received from the host computer (step S1-6). When such order information has been received, the CPU 401a specifies the type of reagent and amount of the reagent to be aspirated according to the analysis item of the sample included in the order information (step S1-7). The data, which includes the reagent type and the amount of reagent to be aspirated according to the analysis item, are stored on the hard disk 401d of the control device 4 beforehand by the operator. The CPU 401a specifies the type of reagent and reagent aspiration amount according to the sample analysis item included in the order information based upon these data. Then, the CPU 401a sends the order information which includes the information specified in step S1-7 to the controller 25a of the measuring unit 2 (step S1-8). Furthermore, this order information also includes the sample aspiration amount, sample heating time and the like.

The operator may also input a direct order by operating the keyboard of the control device 4. In this case, the operator inputs a sample ID and analysis item, and this information is stored on the hard disk 401d. Then, when the barcode reader reads the barcode, the analysis item corresponding to the sample ID included in the barcode information can be read from the hard disk to obtain the order.

Thereafter, the CPU 25a of the measuring unit 2 determines whether or not the order information has been received from the CPU 401a (step S2-4). When the order information has been received, the received order information is stored in the RAM 25c (step S2-5). Then, the CPU 25a controls the sample dispensing arm 30 to aspirate a predetermined amount of the sample from the test tube 150, and move the sample dispensing arm 30 above the cuvette 152 which is loaded in the secondary dispensing table 24 of the rotating part 20. Thereafter, the CPU 401a performs the primary dispensing process by discharging the sample into the cuvette 152 loaded on the primary dispensing table 24 via the sample dispensing arm 30 (step S2-6).

Next, the CPU 25a rotates the primary dispensing table 24 to move the cuvette 152 containing the sample to a position at which the sample can be measured by the HIL detecting part 40. Thus, the sample is optically measured by the HIL detecting part 40 to obtain the optical information (first optical information) from the sample in step S2-7.

Subsequently, the CPU 25a controls the sample dispensing arm 30 so as to aspirate a predetermined amount of the sample from the cuvette 152 held by the holder 24a of the primary dispensing table 24. Thereafter, the CPU 25a performs a secondary dispensing process by controlling the sample dispensing arm 30 to discharge predetermined amounts of the sample specified in the order information into a plurality of cuvettes 152 on the secondary dispensing table 23.

Then, the CPU 25a heats the dispensed sample for the time specified in the order information (step S2-9). This heating time will differ depending on the measurement item, and is normally one to three minutes.

Thereafter, the CPU 25a sets the target temperature of the heater 64 by substituting the reagent aspiration amount specified in the order information into the relational equation (the equation representing the relationship between the reagent aspiration amount and the target temperature of the heater 64) stored in the flash memory 25b (step S2-10).

Then the CPU 25a controls the heater drive circuit 26 to drive the heater 64 and controls the reagent dispensing arm 60 to aspirate the reagent within a reagent container (not shown in the figure) loaded in the reagent tables 21 and 22, and add the aspirated reagent into the sample in the cuvette 152 on the secondary dispensing table 23 (step S2-11). Thus, a measurement sample is prepared. Then the CPU 25a controls the cuvette transporter 70 to move the cuvette 152 containing the measurement sample from the secondary dispensing table 23 to an insertion hole 81a of the cuvette loader 81 of the detecting part 80.

Next, the CPU 25a optically measures (main measurement) the measurement sample in the cuvette 152 via the detector 82 of the detecting part 80 to obtain optical information (second optical information) from the measurement sample. The CPU 25a sends the first optical information obtained in step S2-7 and the second optical information obtained in step S2-12 to the control device 4 (step S2-13).

The CPU 401a of the control device 4 determines whether or not optical information has been received from the CPU 25a (step S1-9). When optical information has been received, the received optical information is analyzed (step S1-10). Furthermore, after the analysis, obtained analysis results are displayed on the display part 4b of the control device 4. Next, the CPU 401a determines whether or not a shutdown command has been received from the operator (step S1-11). When a shutdown command has been received, a shutdown signal is sent to the CPU 25a of the measuring unit 2 (step S1-12). When a shutdown command has not been received, the CPU 401a moves to the process of step S1-2.

The CPU 25a of the measuring unit 2 determines whether or not a shutdown command has been received from the CPU 401a (step S2-14). When a shutdown command has been received, the measuring unit 2 executes shutdown (step S2-15). When a shutdown command has not been received, the CPU 25a moves to the process of step S2-2. Thus, the sample analysis operation of the sample analyzer 1 is completed.

Although a configuration is described in the present embodiment in which a target temperature is adjusted in accordance with the amount of reagent so as to control the amount of heat generated by a heater in accordance with the difference between the reagent temperature and the target temperature, the present invention is not limited to this configuration inasmuch other configurations are possible insofar as the configuration controls the amount of heat generated by heaters in accordance with the amount of reagent; for example, a plurality of heaters may be provided and the number of heaters being driven may be adjusted in accordance with the amount of reagent. Although the present embodiment has been discussed in terms of a configuration in which the heater is controlled by PWM control, the present invention is not limited to this configuration inasmuch as the heater may also be controlled by PAM control (pulse width modulation), or the heater may be controlled by a hybrid inverter method combining both PWM and PAM.

Although the present embodiment has been discussed in terms of a configuration in which a target temperature is set for a heater 64 by substituting a reagent aspiration amount in a relational equation stored in a flash memory 25b, the present invention is not limited to this configuration inasmuch as, for example, table format data associating reagent types and target temperatures may be pre-stored in the flash memory 25b, so as to set the target temperature of the heater 64 based on the table format data and the reagent type included in the order information.

Although the present embodiment has been discussed in terms of a configuration in which the type of reagent and the reagent aspiration amount corresponding to sample analysis item included in the order information is specified by the CPU 401a of the control device 4, the present invention is not limited to this configuration inasmuch as the type of reagent and the reagent aspiration amount may also be specified by the CPU 25a of the measuring unit 2.

Although the present embodiment has been discussed in terms of a configuration in which a target temperature is set for a heater 64 by substituting a reagent aspiration amount in a relational equation stored in a flash memory 25b, the present invention is not limited to this configuration inasmuch as, for example, the target temperature of the heater 64 may also be set based on the sample analysis item alone when the reagent type or the reagent aspiration amount corresponds 1-to-1 to the analysis item of the sample.

Although the syringe pump 67 for aspirating and discharging reagent is provided within the reagent dispensing arm 60 in the present embodiment, the present invention is not limited to this configuration inasmuch as the syringe pump 67 for aspirating and discharging reagent may also be provided outside the reagent dispensing arm 60.

What is claimed is:
1. A dispenser, comprising:
a liquid holder configured to aspirate an amount of liquid and hold the aspirated liquid for later discharge of at least some thereof;
a heater for heating the aspirated liquid held by the liquid holder to a predetermined temperature;
a temperature sensor for detecting a temperature of the aspirated liquid held by the liquid holder;
a heater driver configured to supply an amount of energy to the heater, which is a function of a difference between a target temperature and a temperature detected by the temperature sensor; and
a controller configured to generate the target temperature for the heater driver, the target temperature being different from the predetermined temperature and a function of an aspiration amount of liquid, wherein the controller controls the operation of the heater driver so as to heat the aspirated liquid held by the liquid holder to the predetermined temperature in a time period substantially constant, regardless of the aspirated amount of the liquid, so as to heat the aspirated liquid held by the liquid holder to the set temperature for a substantially constant time period, regardless of the aspirated amount of liquid.

2. The dispenser of claim 1, wherein the liquid holder is a pipette for holding a reagent as the liquid, and the heater is disposed in the pipette.

3. The dispenser of claim 1, wherein the controller generates the target temperature by referencing at least one of an equation and reference table indicative of a relationship between the aspiration amount of the liquid and the target temperature, which yields the target temperature, which generally becomes higher as the aspiration amount becomes larger.

4. The dispenser of claim 3, wherein the relationship yields the target temperature, which becomes higher as the aspiration amount becomes smaller where the aspiration amount is small.

5. The dispenser of claim 3, wherein the relationship expresses the target temperature in ratios to the target temperature of a reference aspiration amount.

6. The dispenser of claim 2, wherein the pipette comprises:
   a distal end having an opening for aspirating and discharging the reagent;
   a small diameter section having a reagent channel for holding the aspirated reagent therein, which goes through inside the small diameter section and communicates with the opening of the distal end; and
   a large diameter section having a diameter larger than that of the small diameter section.

7. The dispenser of claim 6, wherein the heater is disposed along the reagent channel in the pipette avoiding a vicinity of the opening of the distal end.

8. The dispenser of claim 1, wherein the liquid holder discharges at least some of the aspirated liquid before the temperature detected by the temperature sensor becomes levels off.

9. A reagent dispenser, comprising:
   a reagent pipette configured to aspirate an amount of reagent and hold the aspirated reagent for later discharge of at last some thereof;
   a heater for heating the aspirated reagent held by the reagent pipette to a predetermined temperature;
   a temperature sensor for detecting a temperature of the aspirated reagent held by the reagent pipette;
   a heater driver configured to supply an amount of energy to the heather, which is a function of a difference between a target temperature and a temperature detected by the temperature sensor; and
   a controller configured to generate the target temperature for the heater driver, the target temperature being different from the predetermined temperature and a function of at least one of (i) an amount of the aspirated reagent, (ii) a type of the aspirated reagent and (iii) an analyte in a sample to be analyzed with the aspirated reagent, wherein the controller controls the operation of the heater driver so as to heat the aspirated reagent held by the pipette to the predetermined temperature in a time period substantially constant, regardless of the amount of the aspirated reagent, the type of the aspirated reagent, or the analyte to be analyzed by the aspirated reagent held by the reagent pipette.

10. The reagent dispenser of claim 9, wherein the controller generates the target temperature by referencing at least one of an equation and reference table indicative of at least one of relationships between the amount of the aspirated reagent and the target temperature, between the type of the aspirated reagent and the target temperature and between the analyte to be analyzed with the aspirated reagent and the target temperature, and wherein the type of the aspirated reagent and the analyte to be analyzed with the aspirated reagent are each indicative of an amount of the aspirated reagent.

11. The reagent dispenser of claim 9, wherein the heater is disposed in the reagent pipette.

12. The reagent dispenser of claim 9, wherein the reagent pipette discharges at least some of the aspirated reagent before the temperature detected by the temperature sensor levels off.

13. A sample analyzer, comprising the reagent dispenser of claim 9.

14. The sample analyzer of claim 13, wherein the target temperature generator references at least one of an equation and a reference table indicative of at least one of relationships between the amount of the aspirated reagent and the target temperature of the reagent, between the type of the aspirated reagent and the target temperature and between the analyte to be analyzed with the aspirated reagent and the target temperature, wherein the type of the aspirated reagent and the analyte to be analyzed with the aspirated reagent are indicative of an amount of the aspirated reagent held by the reagent pipette.

15. The sample analyzer of claim 13, further comprising a sample dispenser that dispenses blood as a sample, and a detector that detects optical information related to coagulation of the blood.

16. The sample analyzer of claim 13, further comprising a reagent storing part for storing the reagent to be aspirated in a low temperature.

17. The sample analyzer of claim 14, wherein the relationship between the amount of the aspirated reagent and the target temperature yields the target temperature, which generally becomes higher as the aspiration amount of the reagent becomes larger.

18. The sample analyzer of claim 13, wherein the reagent pipette comprises:
   a distal end having an opening for aspirating and discharging the reagent;
   a small diameter section having a reagent channel for holding the aspirated reagent therein, which goes through the small diameter section and communicates with the opening of the distal end; and
   a large diameter section having a diameter larger than that of the small diameter section.

19. The sample analyzer of claim 18, wherein the heater is disposed along the reagent channel in the pipette avoiding a vicinity of the opening of the distal end.

20. The sample analyzer of claim 13, wherein the reagent pipette discharges at least some of the aspirated reagent before the temperature detected by the temperature sensor levels off.

21. The sample analyzer of claim 17, wherein the relationship between the amount of aspirated reagent and the target temperature yields the target temperature, which becomes higher as the aspirated amount become smaller where the aspirated amount is small.

22. The sample analyzer of claim 13, wherein the heater driver comprises a heater drive circuit.

23. The sample analyzer of claim 13, wherein the heater driver is a software module which implements one of a proportional control method and a PID control method.

24. The sample analyzer comprising the dispenser of claim 1.

* * * * *

UNITED STATES PATENT AND TRADEMARK OFFICE
CERTIFICATE OF CORRECTION

PATENT NO. : 7,850,921 B2
APPLICATION NO. : 11/893919
DATED : December 14, 2010
INVENTOR(S) : Satoshi Iguchi et al.

It is certified that error appears in the above-identified patent and that said Letters Patent is hereby corrected as shown below:

In the Claims

In column 15, claim 9, line 43, before "which is a function of a" replace "heather," with --heater,--.

Signed and Sealed this
Fourteenth Day of June, 2011

David J. Kappos
*Director of the United States Patent and Trademark Office*